United States Patent
Shekalim

(10) Patent No.: US 8,038,650 B2
(45) Date of Patent: Oct. 18, 2011

(54) SLOW RELEASE LIQUID DRUG DELIVERY DEVICE

(75) Inventor: Avraham Shekalim, Nesher (IL)

(73) Assignee: Microsert Ltd., Yokneam (Moshava) (IL)

( * ) Notice: Subject to any disclaimer, the term of this patent is extended or adjusted under 35 U.S.C. 154(b) by 0 days.

(21) Appl. No.: 12/709,525

(22) Filed: Feb. 22, 2010

(65) Prior Publication Data

US 2011/0208122 A1   Aug. 25, 2011

(51) Int. Cl.
*A61M 37/00* (2006.01)

(52) U.S. Cl. .................................. 604/132; 604/149

(58) Field of Classification Search .................. 604/131, 604/150, 151–153, 149, 103.1, 103.2, 132, 604/250; 251/337; 137/67
See application file for complete search history.

(56) References Cited

U.S. PATENT DOCUMENTS

| | | | |
|---|---|---|---|
| 4,351,337 A | 9/1982 | Sidman | |
| 4,428,397 A | 1/1984 | Bron | |
| 4,450,150 A | 5/1984 | Sidman | |
| 4,820,273 A | 4/1989 | Reinicke | |
| 5,061,242 A | 10/1991 | Sampson | |
| 5,163,920 A | 11/1992 | Olive | |
| 5,176,641 A * | 1/1993 | Idriss | 604/133 |
| 5,788,979 A * | 8/1998 | Alt et al. | 424/426 |
| 5,836,935 A | 11/1998 | Ashton | |
| 5,993,414 A | 11/1999 | Haller | |
| 6,024,724 A * | 2/2000 | Lee | 604/132 |
| 6,063,058 A * | 5/2000 | Sakamoto | 604/132 |
| 6,183,461 B1 | 2/2001 | Matsuura | |
| 2003/0014036 A1 | 1/2003 | Varner et al. | |
| 2010/0090152 A1* | 4/2010 | Wex et al. | 251/337 |

FOREIGN PATENT DOCUMENTS

WO   WO 2007009808 A1 *   1/2007

* cited by examiner

*Primary Examiner* — Nicholas D Lucchesi
*Assistant Examiner* — Jenna Zhang
(74) *Attorney, Agent, or Firm* — Mark M. Friedman

(57) ABSTRACT

A drug delivery device is formed from an elastomeric element, including an inflatable drug reservoir and a flexible sleeve, and an insert inserted within the flexible sleeve. The insert cooperates with the flexible sleeve to form an at least partially pressure compensated flow regulating mechanism.

9 Claims, 7 Drawing Sheets

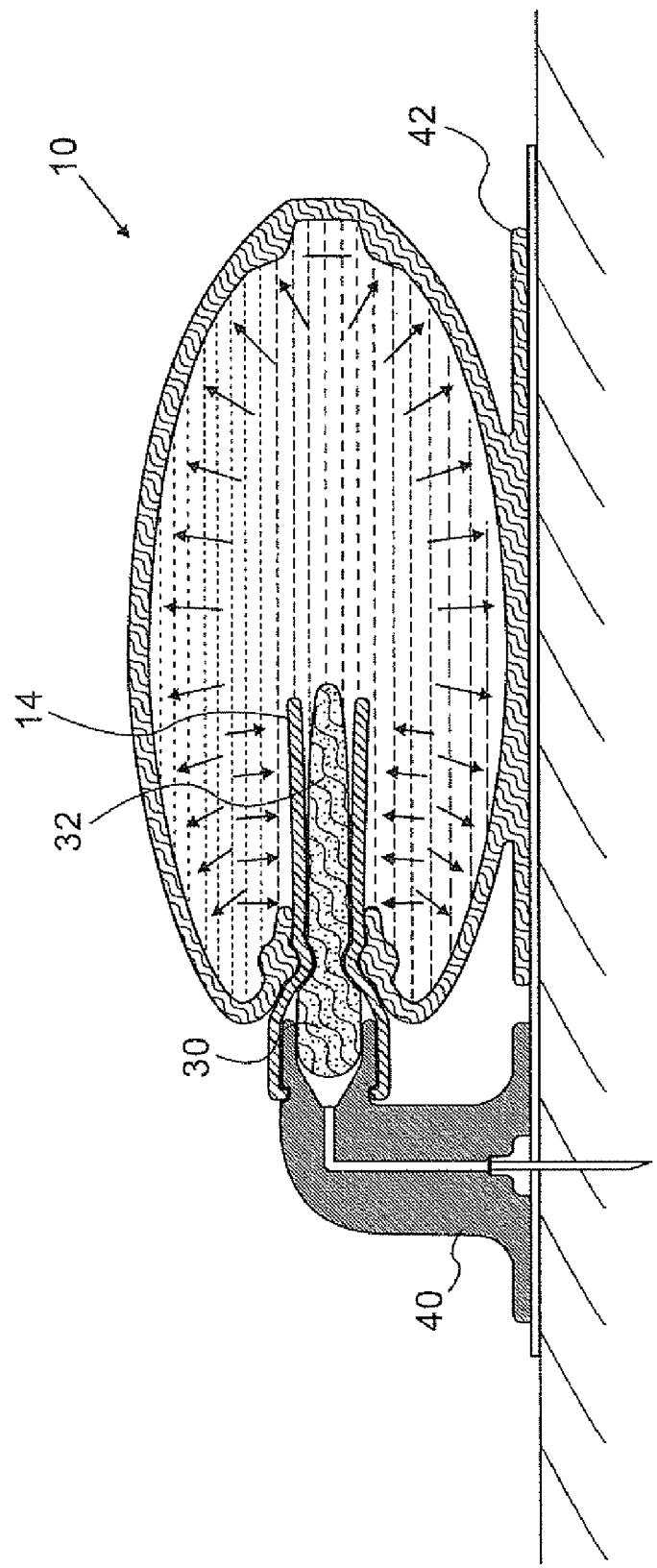

SLOW RELEASE LIQUID DRUG DELIVERY DEVICE

FIELD AND BACKGROUND OF THE INVENTION

The present invention relates to slow release liquid drug delivery devices.

It is known to provide an implantable device which delivers a drug slowly over a period of time. This approach avoids problems of patient compliance, and provides particular advantages where delivery of a drug to a specific target location allows use of much lower overall dosage than would be required for systemic delivery, possibly avoiding undesirable side effects.

In most cases of implantable drug delivery devices, a first surgical procedure is required to implant the device and then another surgical procedure is required to remove the device. Examples of implantable devices for delivery of liquid drugs include, but are not limited to, U.S. Pat. Nos. 5,163,920, 4,428,397, 4,820,273, 5,061,242, 5,993,414, 6,183,461 and 5,836,935.

Notably, U.S. Pat. No. 5,993,414 highlights particular problems encountered when trying to achieve reliable and leak proof weld joints between components.

In order to avoid the need for a second surgical procedure to remove the device, resorbable devices have been proposed. Such devices are generally limited to structures in which the drug is dispersed in a matrix of resorbable material and is gradually released as the matrix breaks down in the body. Examples of this approach may be found in U.S. Pat. Nos. 4,351,337 and 4,450,150 to Sidman. Although this approach has potential advantages, it does not achieve highly uniform drug release rates, and is not suitable for drugs which must be delivered in a liquid form or which have high diffusion rates through the matrix materials.

There is therefore a need for an implantable drug delivery device which would deliver a liquid drug over an extended period at a relatively constant rate without requiring surgical removal of the device after use.

SUMMARY OF THE INVENTION

The present invention is a slow release drug delivery device for implanted or external use.

According to the teachings of an embodiment of the present invention there is provided, a drug delivery device comprising: (a) an elastomeric element comprising: (i) an inflatable drug reservoir, and (ii) a flexible sleeve attached to or integrally formed with the inflatable drug reservoir; and (b) in insert inserted within the flexible sleeve and cooperating therewith to form an at least partially pressure compensated flow regulating mechanism.

According to a further feature of an embodiment of the present invention, the flexible sleeve is integrally formed with the inflatable drug reservoir.

According to a further feature of an embodiment of the present invention, the insert is formed primarily from a porous material.

According to a further feature of an embodiment of the present invention, the insert and the flexible sleeve are configured such that an extent of contact between the flexible sleeve and the insert varies as a function of the pressure within the inflatable drug reservoir.

According to a further feature of an embodiment of the present invention, the insert is formed with an elongated circumferential channel.

According to a further feature of an embodiment of the present invention, the insert is formed primarily from a bioresorbable material.

According to a further feature of an embodiment of the present invention, the elastomeric element is formed from silicone.

According to a further feature of an embodiment of the present invention, the elastomeric element is formed from a bioresorbable material.

According to a further feature of an embodiment of the present invention, the flexible sleeve is deployed primarily within the inflatable drug reservoir.

BRIEF DESCRIPTION OF THE DRAWINGS

The invention is herein described, by way of example only, with reference to the accompanying drawings, wherein:

FIG. 7 illustrates a modified embodiment of the present invention for use as an external drug delivery device.

DESCRIPTION OF THE PREFERRED EMBODIMENTS

An embodiment of the present invention is a drug delivery device with a particularly simple construction, typically formed from a total of only three, or in some cases two, components.

Figure 1A:
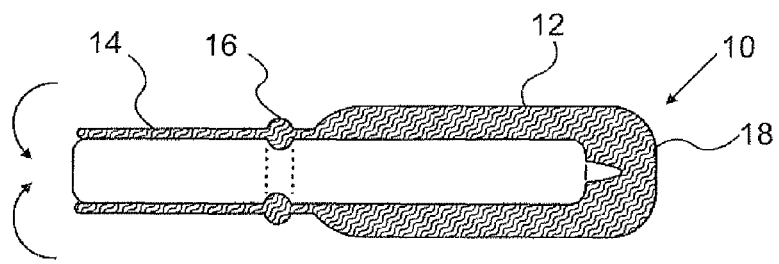
FIG. 1A is a schematic cross-sectional view taken through a bladder-type reservoir from an implantable drug delivery device according to an embodiment of the present invention.
Figure 1B:
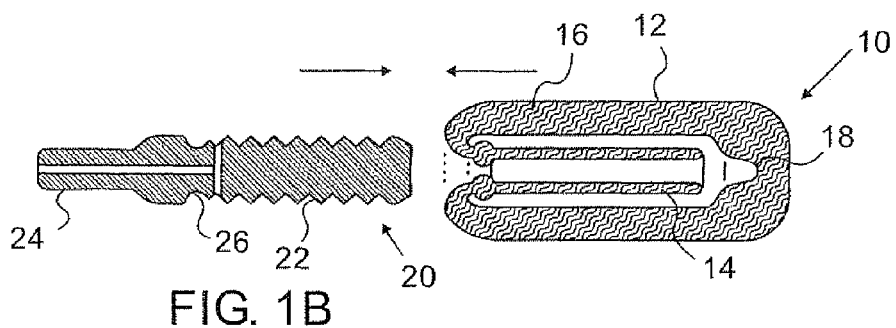
FIG. 1B is a schematic cross-sectional view taken through the bladder-type reservoir of FIG. 1A and an insert for use in an implantable drug delivery device according to an embodiment of the present invention.
Figure 1C:
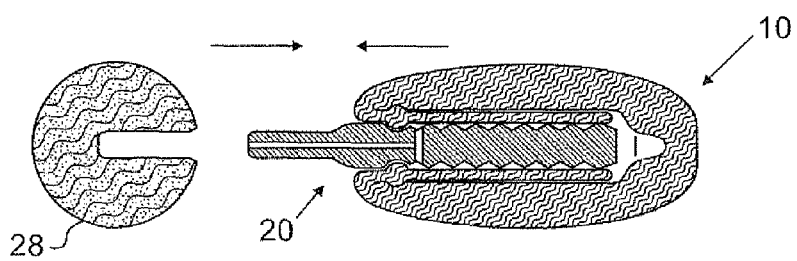
FIG. 1C is a schematic cross-sectional view taken through the bladder-type reservoir and insert of FIG. 1B after assembly, and showing an outlet diffuser for use as part of an implantable drug delivery device according to an embodiment of the present invention.
Figure 1D:
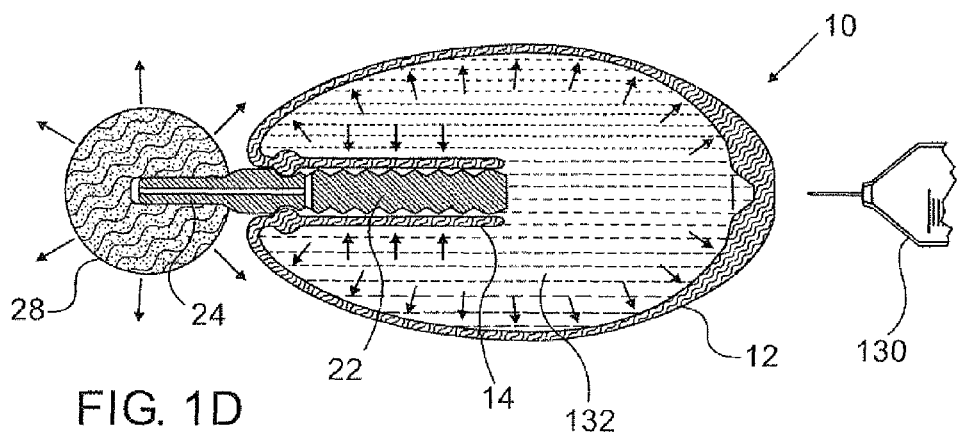
FIG. 1D shows the implantable drug delivery device assembled from the components of FIG. 1C after being filled with a liquid drug.
Figure 2:
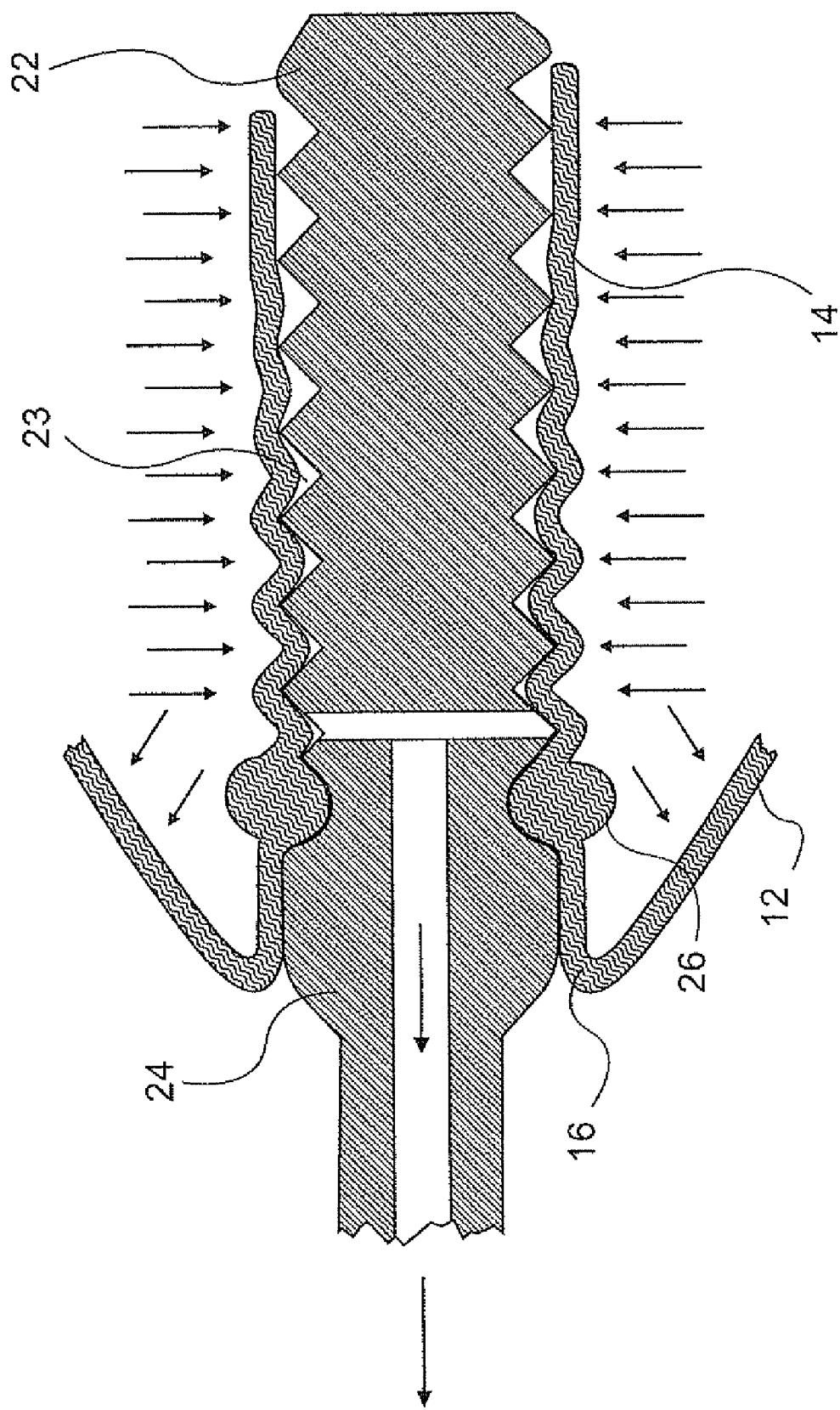
FIG. 2 is an enlarged region of FIG. 1D illustrating a flow regulation/compensation mechanism according to an embodiment of the present invention.

An embodiment of the device illustrated in FIGS. 1A-2 is formed from an elastomeric component 10 which is formed with an inflatable bladder-type reservoir 12 and a regulator sleeve 14. In the preferred case illustrated here, elastomer component 10 also has an integrated retainer bead 16 and a thickened portion defining a pierceable septum 18 for filling or refilling the device.

A second component is an insert 20 which is configured to cooperate with regulator sleeve 14 to define a pressure-compensated flow restriction, thereby regulating a rate of drug release from the device to a relatively constant rate. In the example shown here, insert 20 has a regulator portion 22 formed with a variable geometry helical flow channel 23, described below in more detail with reference to FIG. 2, and an outlet portion 24 defining a flow outlet. A peripheral groove 26 is provided to receive retainer bead 16.

A third component of the device illustrated here is an outlet diffuser 28 in the form of a porous body, here shown as a sphere, which is configured to attach to outlet portion 24.

The drug delivery device is assembled by folding regulator sleeve 14 inwards inside reservoir 12 and introducing insert 20 until retainer bead 16 engages groove 26 to produce the configuration shown in FIG. 1C. Outlet diffuser 28 is attached to complete the device. The device can then be filled (and subsequently refilled) via a needle (shown schematically as syringe 130 in FIG. 1D) inserted through septum 18 to inflate reservoir 12 with a liquid 132 to be delivered. The elasticity of the reservoir acts like a balloon to apply pressure to the contained liquid, thereby driving release of the liquid through the flow regulation mechanism.

According to one non-limiting embodiment, inflatable reservoir 12 may be configured to maintain a relatively constant pressure over a majority of its design volume, as is known in the art. However, the self-compensating flow regulation described herein renders this feature non-critical.

Most preferably, the relaxed state of reservoir 12 closes closely against the regulation mechanism formed by sleeve 14 and regulator portion 22, thereby ensuring a driving pressure for delivering the drug until the reservoir is substantially empty.

Operation of the flow regulation mechanism of this embodiment is best understood with reference to FIG. 2. Helical flow channel 23 together with the inward facing surface of sleeve 14 define an elongated helical channel. Pressure within the reservoir (resulting from the resilient contracting force exerted by the elastomer outer walls) acts on the regulator sleeve 14, trying to force the elastomer sleeve into channel 23. In the region of channel 23 near the beginning of the flow path through the regulation mechanism, the pressure difference between the flow channel and the reservoir pressure is small and only a small deformation of regulator sleeve 14 occurs. As the liquid continues along the long helical path, the pressure gradually drops, leading to a larger pressure differential across the sleeve and tending to conform the sleeve closer to the channel shape. It will be noted that, if the pressure within the reservoir increases, such as from something pressing against the reservoir, sleeve 14 becomes pressed more closely into channel 23 thereby constricting the flow path and compensating for the increased reservoir pressure to maintain a relatively constant outlet flow rate. Conversely, if the reservoir pressure decreases, such as from a drop in ambient pressure at high altitude, sleeve 14 is pressed less closely into channel 23, instead resiliently returning towards its relaxed cylindrical state and thereby reducing constriction of the flow path. In this manner, the flow rate is compensated, rendering it relatively constant under conditions of varying reservoir pressure.

Helical flow channel 23 is shown here as a uniform cross-section channel. However, it will be noted that channel 23 may optionally be formed with a variable depth and/or shape along its length so as to modify and improve the uniformity of the flow compensation. For example, in some cases, it may be desirable that the region closer to the inlet end (the right hand side as shown in FIG. 2) is deeper and/or narrower and the channel 23 becomes progressively shallower and/or wider towards the outlet.

Optionally, channel 23 may be shaped to help ensure that the flow path does not become completely sealed, for example, by employing a sharply angled root to the channel. However, it should be noted that this feature is not essential. As already explained, regulation is achieved as a result of pressure difference between the reservoir and the flow path. In any situation where the flow path were to become momentarily blocked, the static pressure along the flow path up to the blockage would quickly equalize, thereby applying the full intra-reservoir pressure directly at the point of blockage so as to clear the blockage. As a result, self-blocking of the regulation mechanism is typically avoided in all cases.

It is a particularly preferred feature of certain implementations of the present invention that the device need not be surgically removed on completion of its drug delivery function. To this end, part or all of the device may be made from bioresorbable materials which degrade over time and are absorbed into the body tissue or otherwise disposed of by natural body processes. In particular, certain preferred implementations have insert 20 and/or outlet diffuser 28 formed from bioresorbable material. Examples of suitable bioresorbable materials include, but are not limited to biodegradable polymers such as poly(lactic acid), poly(glycolic acid), poly (ortho ester), and polyanhydrids, as well as copolymers of these materials. Clearly, the rate of degradation must be chosen to be slow relative to the planned functional lifetime of the device. Choice of a suitable composition with a corresponding degradation rate suitable for any given implementation is well within the skill of one ordinarily skilled in the art.

Regarding production of porous polymer materials from biodegradable and other polymer materials, various production techniques and corresponding products are commercially available. Examples of commercial sources for such materials include, but are not limited to, Porex Technologies Inc. (GA, USA) and MicroPore Plastics Inc. (GA, USA).

Where insert 20 and outlet diffuser 28 are formed from biodegradable materials, elastomeric component 10 may be formed from an inert non-biodegradable material such as silicone rubber. The empty squashable structure of the collapsed reservoir remaining after full degradation of the other components is believed to be physiologically acceptable when left subcutaneously for an indefinite period.

Alternatively, elastomeric component 10 may also be formed from a biodegradable elastomer to provide a fully biodegradable product. A non-limiting example of a suitable bioresorbable elastomer is poly(glycerol-sebacic acid) ("PGS").

Although illustrated here in a preferred implementation in which reservoir 12 and sleeve 14 are integrated as part of a single elastomeric component, alternative embodiments in which reservoir 12 and sleeve 14 are separate elements subsequently fastened together or clamped together during use also fall within the scope of the present invention.

Furthermore, although illustrated here in a preferred implementation in which flow regulation is performed by deformation of sleeve 14 against insert 20, alternative embodiments in which a self-contained flow regulator (not shown) is inserted within sleeve 14 and sleeve 14 itself does not perform an active role in the flow rate regulation also fall within the scope of the present invention.

Figure 3:
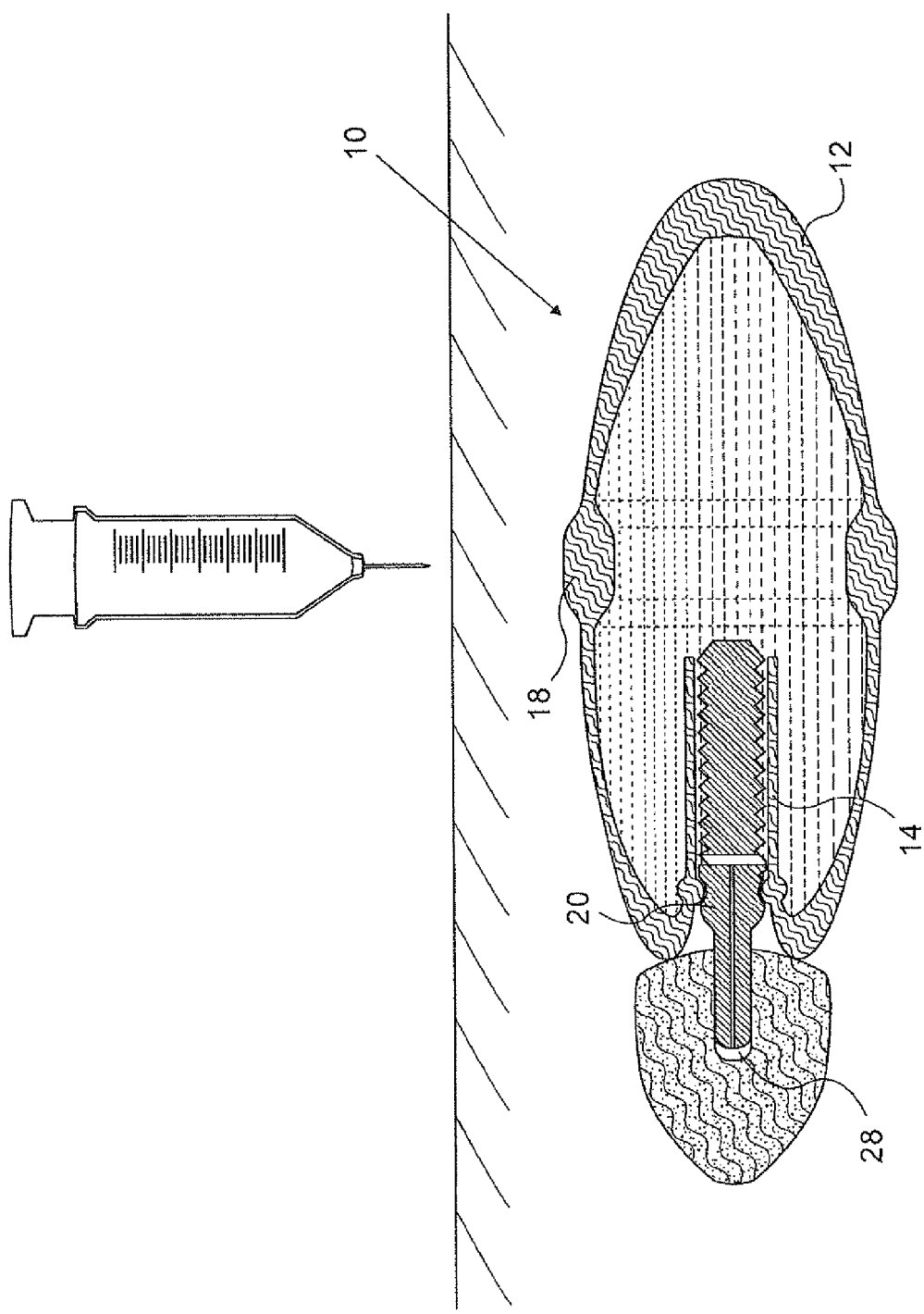
FIG. 3 illustrates a variation of the implementation of FIG. 1D which allows percutaneous refilling of the reservoir while lying transversely beneath the skin of a patient.

Turning now to FIG. 3, this shows a device similar to the device of FIGS. 1A-2, but formed in an elongated shape suitable for implanting lying flat under the skin. To facilitate percutaneous refilling of the device, the device is here formed with a thickened annular septum as a belt around the reservoir, thereby allowing tactile location of the septum and lateral injection directly into the reservoir. In all other respects, the device of FIG. 3 is structurally and functionally analogous to the device of FIGS. 1A-2.

Figure 4:
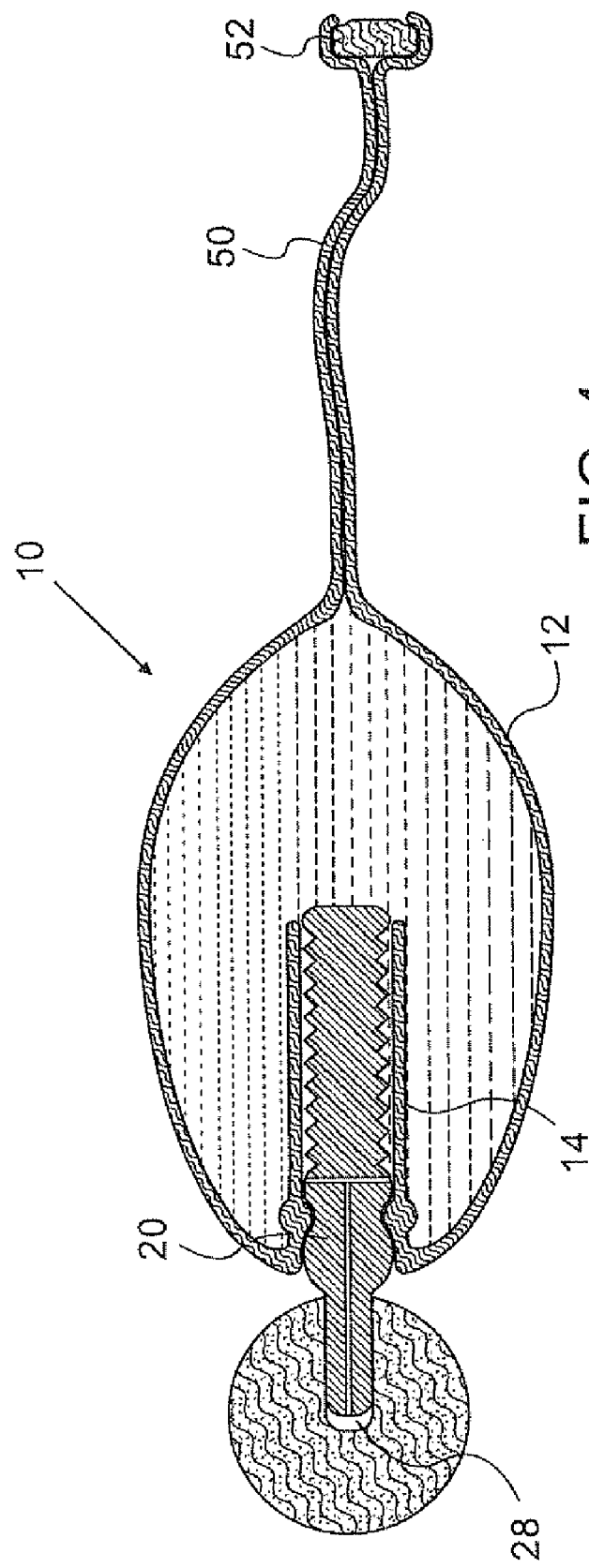
FIG. 4 illustrates a further variation of the implementation of FIG. 1D in which the reservoir is integrally formed with a filling tube that terminates in a remote septum, allowing percutaneous refilling of the reservoir for a drug delivery device deployed in an inaccessible location within the body of a patient.

Turning now to FIG. 4, this shows a device similar to the device of FIGS. 1A-2, but in which the inflatable bladder-type reservoir is integrally formed with a filling tube 50 which terminates in a refilling port with a septum 52. By suitable choice of wall thickness and tube diameter, it is possible to form the refilling tube from the same elastomer material as used for the reservoir while ensuring that it does not dilate under the pressures used to inflate the reservoir with a drug. As a result, substantially all of a drug injected through the refilling septum is transferred directly into the reservoir. This configuration allows deployment of the drug delivery device in proximity to a deep body target region while maintaining percutaneous accessibility for refilling. The parts of the device are typically secured in situ by appropriate stitching of adjacent tissue, as is well known in the art. In all other respects, the device of FIG. 4 is structurally and functionally analogous to the device of FIGS. 1A-2.

Figure 5:
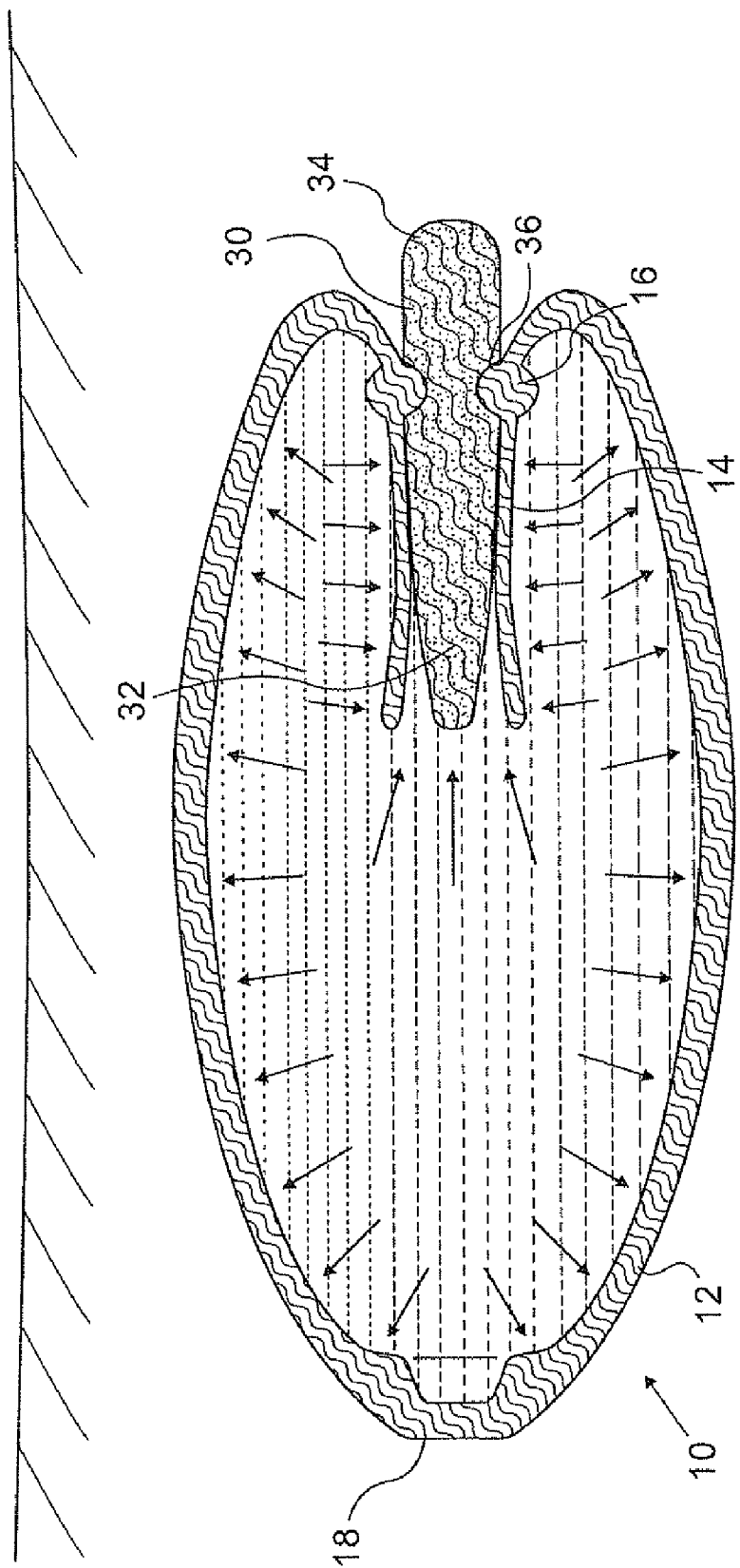
FIG. 5 illustrates an implantable drug delivery device according to an alternative embodiment of the present invention employing a porous insert as part of a flow compensation mechanism.
Figure 6:
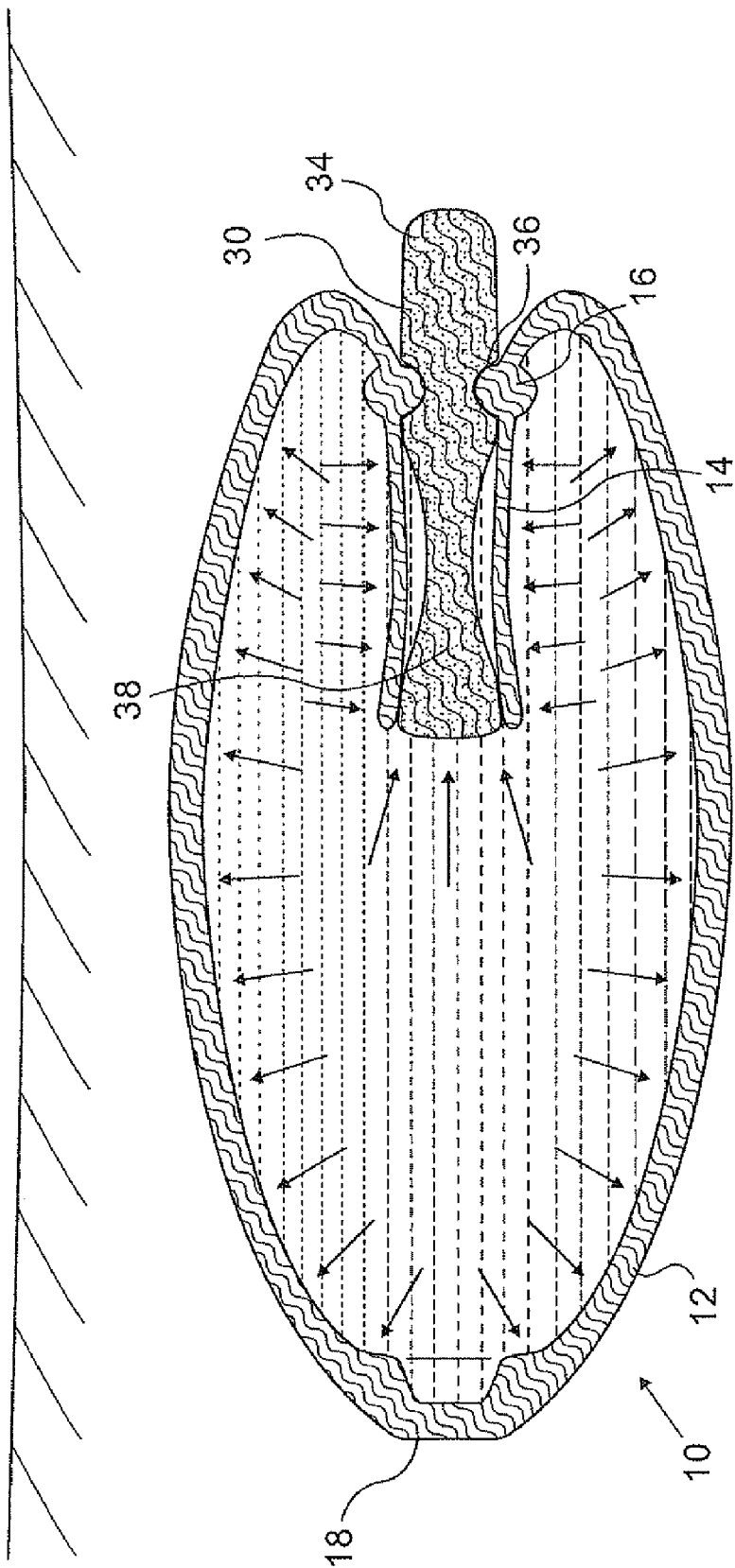
FIG. 6 illustrates an embodiment similar to FIG. 5 but employing a variant form of the porous insert.

Turning now to FIGS. 5 and 6, there are shown additional embodiments of a drug delivery device according to an aspect of the present invention. These devices are conceptually and structurally similar to the devices described above, but employ a porous insert to define at least part of the flow regulation mechanism. Specifically, referring first to FIG. 5, there is shown a device in which elastomeric component 10 is essentially the same as described earlier (including inflatable bladder-type reservoir 12, regulator sleeve 14, integrated retainer bead 16 and pierceable septum 18). In this case, insert 20 described above is replaced by a porous insert 30 which has a generally conical regulating portion 32, an outlet portion 34 and a peripheral groove 36. The porous material of insert 20 provides a flow restriction, defining a limited rate of release of the liquid contents of reservoir 12. Flow regulation is achieved by pressure-responsive closing or opening of regulator sleeve 14 against the surface of the conical regulating portion, thereby forcing the liquid flow to pass through a longer or shorter path via the porous material as a function of the pressure differential between the reservoir and liquid along the flow path.

FIG. 6 shows a similar device in which regulating portion 38 of porous insert 30 has a generally hour-glass shape, ensuring that there is a significant initial pressure drop near the beginning of the flow path through the porous material. Here too, flow regulation/compensation is achieved by the pressure differential causing a variable degree of closure of the regulator sleeve against the narrower portion of the insert, thereby defining a relatively longer or shorter length of flow path along which the flow can bypass the porous material and find a lower flow impedance path.

It should be noted that, in all other respects, the embodiments of FIGS. 5 and 6 are similar to the previously described embodiments, and can be implemented with any and all of the various features described above with reference to FIGS. 1-4. Similarly, these embodiments can be implemented as partially or fully resorbable structures. Typically, due to the inherent diffuse release properties of the porous insert 30, no additional outlet diffuser is required.

Finally, turning briefly to FIG. 7, it should be noted that the various embodiments of the invention described herein are not limited to implantable drug delivery devices and can also be implemented to advantage in external drug delivery devices. By way of one non-limiting example, FIG. 7 illustrates a device similar to that of FIG. 5 provided with a needle adapter 40 and adhesive pad 42 for use as an externally skin-mounted drug infusion device. It will be appreciated that this option may be implemented with any and all of the embodiments described herein, or combinations thereof.

It will be appreciated that the above descriptions are intended only to serve as examples, and that many other embodiments are possible within the scope of the present invention as defined in the appended claims.

What is claimed is:

1. A drug delivery device comprising:
   (a) an elastomeric element comprising:
      (i) an inflatable drug reservoir, and
      (ii) a flexible sleeve attached to or integrally formed with said inflatable drug reservoir; and
   (b) an insert inserted within said flexible sleeve and cooperating therewith to form an outlet flow path for releasing a drug from said drug reservoir, at least part of said outlet flow path passing between said flexible sleeve and said insert, wherein said flexible sleeve is disposed so as to be acted upon by a pressure within said drug reservoir so as to change a flow impedance of said outlet flow path when the pressure within the reservoir varies, thereby providing an at least partially pressure compensated flow regulating mechanism.

2. The drug delivery device of claim 1, wherein said flexible sleeve is integrally formed with said inflatable drug reservoir.

3. The drug delivery device of claim 1, wherein said insert is formed primarily from a porous material.

4. The drug delivery device of claim 3, wherein said insert and said flexible sleeve are configured such that an extent of contact between said flexible sleeve and said insert varies as a function of the pressure within said inflatable drug reservoir.

5. The drug delivery device of claim 1, wherein said insert is formed with an elongated circumferential channel.

6. The drug delivery device of claim 1, wherein said insert is formed primarily from a bioresorbable material.

7. The drug delivery device of claim 6, wherein said elastomeric element is formed from silicone.

8. The drug delivery device of claim 6, wherein said elastomeric element is formed from a bioresorbable material.

9. The drug delivery device of claim 1, wherein said flexible sleeve is deployed primarily within said inflatable drug reservoir.

* * * * *